United States Patent [19]
Rink et al.

[11] Patent Number: 5,366,456
[45] Date of Patent: Nov. 22, 1994

[54] ANGLE FIRING FIBER OPTIC LASER SCALPEL AND METHOD OF USE

[75] Inventors: John L. Rink; Kwok H. Ngai, both of San Francisco; King J. J. Yu, Oakland; Herrick Tam, San Francisco, all of Calif.

[73] Assignee: Xintec Corporation, Oakland, Calif.

[21] Appl. No.: 14,814

[22] Filed: Feb. 8, 1993

[51] Int. Cl.$^5$ ............................................. A61B 17/36
[52] U.S. Cl. ........................................ 606/16; 606/17; 606/15
[58] Field of Search ..................... 606/14, 15, 16, 17, 606/6, 7

[56] References Cited

U.S. PATENT DOCUMENTS

| | | | |
|---|---|---|---|
| 3,865,113 | 2/1975 | Sharon et al. | |
| 3,865,114 | 2/1975 | Sharon et al. | |
| 4,266,547 | 5/1981 | Komiya | |
| 4,266,549 | 5/1981 | Kimura | |
| 4,313,431 | 2/1982 | Frank | 606/16 |
| 4,458,683 | 7/1984 | Katsuyoshi | 128/395 |
| 4,492,230 | 1/1985 | Sunago et al. | |
| 4,517,973 | 5/1985 | Sunago et al. | |
| 4,760,840 | 8/1988 | Fournier, Jr. et al. | 606/15 |
| 4,791,927 | 12/1988 | Menger | |
| 4,950,268 | 8/1990 | Rink | 606/12 |
| 5,057,099 | 10/1991 | Rink | 606/12 |
| 5,061,265 | 10/1991 | Abela et al. | 606/15 |
| 5,061,266 | 10/1991 | Hakky | 606/15 |
| 5,095,889 | 3/1992 | Weissmuller et al. | 606/16 |
| 5,163,935 | 11/1992 | Black et al. | 606/17 |
| 5,242,438 | 9/1993 | Saadatmanesh et al. | 606/15 |
| 5,246,436 | 9/1993 | Rowe | 606/17 |
| 5,257,991 | 11/1993 | Fletcher et al. | 606/16 |

OTHER PUBLICATIONS

McCann, Brian P.; "Fiber Holds the Key to Medical Lasers' Success"; *Photonics Spectra;* May 1990; pp. 127–136.
Stein, Barry, "Transurethral Resection of Benign Prostatic Hyperplasia with Advanced Nd: YAG Laser Surgical Systems".
Product Information–BARD ®; "Urolase TM Right Angle Laser Fiber"; Part No. 350000.
Product Information–Cytocare; "ProLase II".
Product Information–Laserscope Surgical Systems; "Angled Delivery Device"; Part No. 10-2071.
Product Information–LaserSonics; "UltraLine TM Lateral Firing Quartz Fiber".
Product Information–LaserSonics; "ArthroGuide TM $CO_2$ Laser Fiber Delivery System".

*Primary Examiner*—Stephen C. Pellegrino
*Assistant Examiner*—Sonya C. Harris
*Attorney, Agent, or Firm*—James J. Leary; Ray K. Shahani

[57] ABSTRACT

The present invention relates generally to a laser cutting scalpel for use in medical and other applications, and more particularly, to such an apparatus wherein the transmitted radiation is delivered at an angle to the incident radiation source and tool. The invention is capable of coagulating, cutting or vaporizing tissue and may be useful in a wide range of surgical and non-surgical applications. The device has a firing tip which has an insert with a highly polished mirrored surface lying at a specific angle with respect to the central longitudinal axis of the optical fiber. Thus impinging laser radiation is reflected to the side and delivered at approximately a right angle to the fiber. The invention also features one or more cooling vents located in the firing tip itself resulting in a device less prone to failure during operation. The device can be positioned accurately with respect to depth of insertion of the fiber. Another embodiment features the firing tip mounted on the tip of a cannula, the entire apparatus being rotatable about the central axis of the fiber allowing the surgeon to direct the angle of fire toward specific points during the operation.

22 Claims, 6 Drawing Sheets

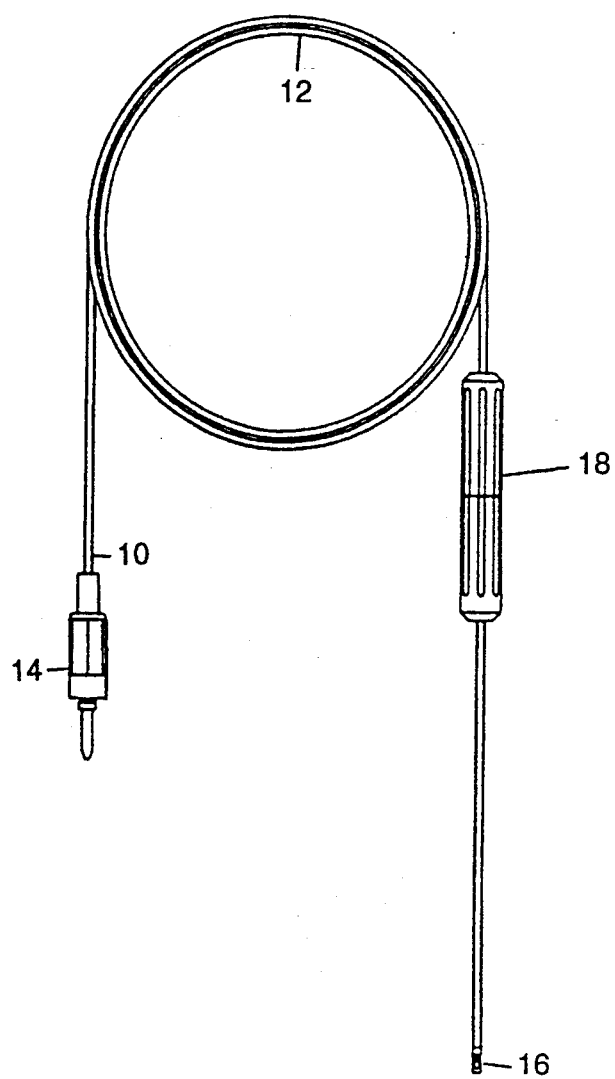
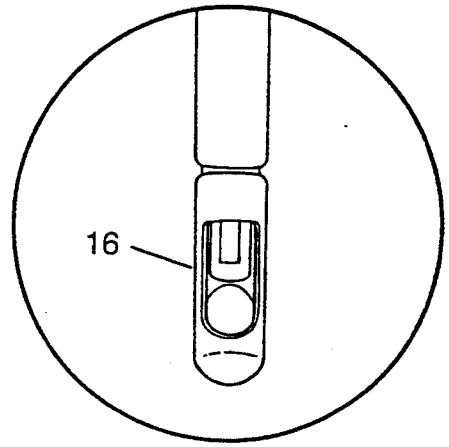
FIG. 1A
FIG. 1B

ANGLE FIRING FIBER OPTIC LASER SCALPEL AND METHOD OF USE

FIELD OF THE INVENTION

The present invention relates generally to a laser cutting scalpel for use in medical and other applications, and more particularly, to such an apparatus wherein the transmitted radiation is delivered at an angle to the incident radiation source and tool. The invention is capable of coagulating, cutting or vaporizing tissue and may be useful in a wide range of surgical and non-surgical applications.

BACKGROUND OF THE INVENTION

Although the first useful lasers were developed in the 1960s, recent advances in laser and fiber optic delivery systems have greatly enhanced the use of this technology in the field of medicine. Today there are numerous types of laser systems designed for operation in a wide range of applications primarily related to surgical procedures.

A common type of laser known as a CO2 laser delivers radiation with a wavelength of 10.64 microns. However, in order to focus or channel the radiation produced by a CO2 laser it is necessary to configure sets of mirrors in certain ways. These systems are typically large and expensive. With the advent of the YAG type laser, it became possible to generate and focus the 1.064 micron wavelength laser radiation through a silica core optical fiber. Thus, fiber optic surgical tools have become standard in certain procedures and the range of their utility is still being explored and discovered.

Laser scalpels are used in different ways, including incision, necrosis or killing of live tissue, removal of tissue or structure, and cauterization of tissue. During incision and removal of tissue, a beam of laser radiation causes an instantaneous vaporization of the water molecules in the tissue contacted by the beam. The tissue seems to disappear with a puff of steam, leaving behind a very small amount of charred tissue. This process is called ablation, or more specifically photoablation, a term which refers to the removal of live, diseased or dead tissue by vaporization. Incision is accomplished using a very narrow beam directed to a small point drawn across the tissue being incised. A very focused beam would provide the greatest amount of control during either operation.

Cauterization and necrosis of living tissue is accomplished or coagulation, more specifically, by photocoagulation of contacted or penetrated tissue. In this modality, the laser beam causes the proteins in the contacted tissue to heat up rapidly and thermally denature. This essentially kills and seals living tissue and blood vessels. The process has been likened to frying an egg. In practice, during an incision procedure cauterization of the incised tissue is likely to occur simultaneously. Thus, laser surgery is often characterized by a lack of bleeding during the operation.

The process which occurs during an operation depends upon the technique and the type of radiation being used. Typically, although light at 10.64 is strongly absorbed by the H2O molecule resulting in efficient incision or ablation of tissue, a surgeon may be able to defocus the light beam and decrease the intensity of the radiation, with a resulting effect of cauterization. Similarly, a YAG type laser can be used to cauterize. Since light at 1.064 microns is not strongly absorbed by water molecules the radiant energy scatters and overall surface coagulation would occur. However, a fiber optic delivery system is capable of creating a very small focal point with a very narrow beam, and therefore, incision or ablation is also possible.

In the prior art there are described devices which generate a dual wavelength beam of radiation and are thereby capable of both cutting and cauterizing. There also exist inventions which deliver energy at much shorter wavelengths, such as 250-350 nm. At these wavelengths proteins, as opposed to water molecules, absorb the radiation. These systems, however, are less suitable for general types of surgical operations since they are more complicated to operate. Use of such systems has not become standard in most medical facilities and their cost is generally too high to justify their purchase for occasional use in fairly specialized procedures.

The construction of optical fibers used in surgical procedures is fairly simple. A plastic or silicone cladding is often used to protect the quartz fiber which itself transmits the laser radiation. Transmission of the radiant beam is possible since the beam is constrained to the core of the fiber. Very few photons escape the fiber. The technology related to the use of silica fibers in medical lasers is well known, e.g. B. P. McCann, Photonics Spectra, May 1990, pp 127-136. Differences between these types of optical fibers and those used in telecommunications and data transmission are important. Several design factors must be considered such as sterilizability, quartz core integrity and purity, power capacity and index of refraction of materials of construction.

Generally, 20 to 100 watts of energy are used to perform soft tissue surgery. A scalpel used externally might be operated in a much different manner than a scalpel used in internal surgery. An angle firing apparatus is very important when a cystoscope or other type of endoscope is used. The scalpels used with most types of endoscopes are very small. Additionally, often laser surgery is performed with irrigation by a cooling gas or liquid to cool the scalpel firing tip as well as to prevent the tissue from overheating. Internal surgery techniques generally use liquids, such as a saline solution. Additionally, liquids are more practical since containment of gases poses certain restrictions tool design. Therefore, often a cystoscope will have multiple channels or will be large enough to accommodate a viewing port or camera, a scalpel, an irrigation supply and vacuum channel to remove the coolant.

Delivery of high power radiation can have a very damaging effect on the scalpel itself. One of the problems with existing designs is that the tip which directs the laser beam at a right angle becomes overheated. This is caused by an absorption of power (heat) at the reflecting surface. Overheating of the firing tip can be caused by fouling of the firing tip itself, an accumulation of incompletely burned tissue which rapidly heats up and can trigger a process known as thermal runaway. As heat rapidly builds up the firing tip melts or crumbles away. Often, angle firing surgical scalpels will need to be replaced partway through the surgical operation due to this problem.

Thermal runaway can be avoided by providing a transparent, hard tip, such as sapphire or quartz. An alternative is to provide a highly reflective surface in the scalpel tip for directing the beam. One material capable of being polished to a very high reflectance is gold. Other materials could be used. If more of the incident radiation is reflected less will be absorbed and the temperature at the surface will not rise too high, especially using today's advanced lasers with pulsed energy, high-peak pulsing and temperature detecting fiber tip protection systems. Additionally, encasing the firing tip in some more durable material, such as stainless steel, would help preserve firing tip integrity. In the prior art, the reflective surface is part of the firing tip and is therefore difficult, if not impossible, to polish.

Another solution to the problem of thermal instability is to provide at least one vent or hole in the firing tip of the scalpel. As the reflected beam is directed to the side, steam is generated by the cooling irrigation fluid in a direction normal to the reflected surface (the hot surface). Providing convection cooling vents on the side opposite the opening for the reflected beam will draw the cooling solution into the firing tip of the scalpel and increase heat dissipation from the firing tip. In operation the cooling fluid would have the effect of cooling both the firing tip and the tissue directly in beam contact.

A scalpel which could be adjusted to provide the precise amount of cooling ability would be very useful. For example, if during a single operation, the surgeon first wished to coagulate a large amount of tissue, an instrument which delivered lower power radiation for relatively long periods of time would need to be well irrigated to prevent overheating from extended use. Thus large cooling vents could be necessary in the firing tip of such a scalpel. Then, to vaporize the tissue the surgeon could increase the power output of the scalpel and vaporize the coagulated tissue in short duration, high powered operation. Unless the flowrate of cooling water could be reduced, the vaporization step would be impossible. As described above, the two different processes of coagulating and ablation require different surgical operating parameters.

Another problem associated with current laser scalpels is that they are often clumsy to use and difficult to manipulate precisely. One problem is that the quartz fiber is so thin it is difficult to grasp effectively, especially if it is used in conjunction with a cystoscope or some type of endoscope where the firing end cannot be controlled directly by the surgeon. Also, as the scalpel is rotated and manipulated by the surgeon, the fiber becomes twisted under a certain amount of angular torque. It would be desirable to provide a scalpel which would be easily controlled, perhaps through the use of some external control means.

Many surgical operations are standard and the procedures followed are routine and well known in the field. For example, in prostate surgery to reduce an enlargened prostate, a typical surgical procedure using a laser scalpel would be to fire energy at four specific anatomic zones causing ablation in very precisely delimited areas in the prostate gland itself. Since the four points procedure is common it would be desirable to provide the surgeon with a scalpel which would select consecutively the exact points of laser beam contact, making the operation safer and less prone to surgeon error.

The following describes the method for performing a prostatectomy, the removal of tissue from an enlarged prostate gland. Using a laser scalpel, the tissue to be removed is coagulated to kill the tissue. This results in an immediate swelling of the surrounding tissue. Therefore, a catheter is allowed to remain in place for several days following the operation to allow for drainage of urine. Once the swelling subsides, the catheter is removed and over a period of several weeks the dead tissue sloughs off naturally. It would be desirable to provide a scalpel which would allow the surgeon to remove the swollen, coagulated tissue by vaporization during the same operation to avoid the need for a catheter completely. As discussed above, radiation at 1.064 microns is not readily absorbed by water molecules. It appears that the high-peak power output laser is capable of generating higher temperatures useful for vaporization at the surface.

It would be desirable to have an angle firing scalpel which would not overheat and lose integrity and efficiency. It would also be desirable to have an angle firing scalpel which could both cut tissue and perform the cauterization process, either simultaneously or by the surgeon's control. Such a scalpel should be appropriately sized to be convenient to use. It is believed that the present invention meets these needs.

SUMMARY OF THE INVENTION

This invention is an improved angle firing fiber optic laser scalpel. In the prior art, the causes of fiber tip overheating damage can be attributed to at least three factors: (1) inefficiency of the reflection of the laser energy, (2) inefficient cooling of the firing tip, and (3) poor structural design of the firing tip.

An insert is used in the firing tip of the present invention. The insert is made out of gold or some other material which can be polished very highly. The insert could also have a coating or layer of reflective material applied to it. The insert can be polished before it is inserted into the firing tip. Thus, the precise angle at which the laser beam is directed, whether it be greater, equal to or less than 90 degrees to the incident beam, can be specified by the manufacturer.

Also, the optical surface of the insert can be given a curvature for focusing the beam. The region in which a laser beam is focused will be the hottest but other points in the beam path are useful for deep tissue coagulation or surface cauterization. Thus, firing tips can be manufactured with inserts with concave reflecting surfaces with varying focal lengths which will provide a greater range of precision instruments. The surgeon can select the tool depending on the focal point desired and use the same instrument to incise, remove tissue or cauterize.

Since the firing tip itself need not be made entirely out a material which will take a high polish, it can be made out of some more durable material, such as stainless steel. Thus the firing tip will be more resistant to thermal decay than scalpels currently being used. Additionally, since the firing tip is stronger it is possible to provide at least one cooling vent in the firing tip without sacrificing mechanical strength. These venus would allow for enhanced convection cooling capacity. They could also be adjustable to provide a variable amount of cooling.

It is a further object of this invention to provide the medical practitioner with an instrument which can be manipulated efficiently and precisely. The device can either be mounted directly onto a fiber optic waveguide or at the end of a cannula or other device. This invention can be used for external surgery or internal surgery, for example through the internal lumen of a cystoscope or other type of endoscope.

The scalpel can be operated precisely using a positioning device. This device would be assembled with the optical fiber and would allow the scalpel to be accurately retracted or extended into the region being operated upon. The positioning device can feature a side position indexing mechanism which could be useful in standard operations, for example, in prostate surgery as discussed above, using a channel of a cystoscope or other lumen. This type of device would allow the surgeon to select and maintain the depth to which the scalpel is inserted into the region being operated upon. Then the device would allow the firing tip to be rotated any given position or to certain pre-determined positions.

A novel method for removing tissue is disclosed. The method entails the use of a laser source with a power output regulator and can provide a pulsed, high-peak power output. The tissue is first coagulated and then removed using a higher power output.

BRIEF DESCRIPTION OF THE DRAWINGS

FIG. 1A is a drawing of the present invention with a depth positioning device attached.

FIG. 1B is a front detail view of an embodiment of the firing tip of the present invention.

DETAILED DESCRIPTION OF THE INVENTION

Figure 2:
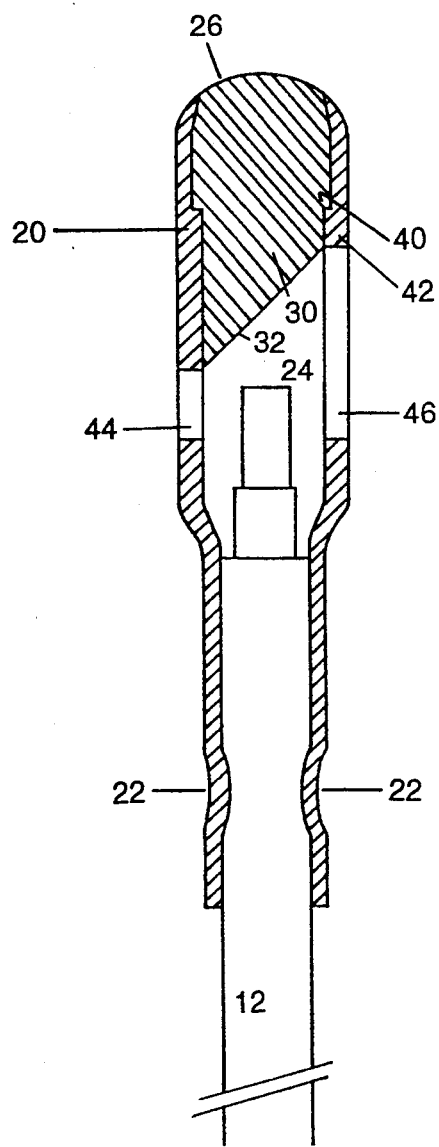
FIG. 2 is a cross section view of the firing tip of one embodiment of the invention.

FIG. 1 is a view of the present invention, a surgical scalpel. At the proximal end 10 of the optical fiber 12 there is a releasable optical fiber connector 14. These connectors are standard in the industry and can also be proprietary. At the distal end 16 of the assembly there is the firing tip 20, shown enlarged.

Also shown is a positioning device 18 for use when the scalpel is operated with a lumen or endoscope or in another type of procedure. The distance through which the scalpel is inserted into a rigid cannula or endoscope can be adjusted and precisely positioned by the surgeon during a surgical operation. The device can be any apparatus which can be precisely positioned on the flexible fiber and will be convenient to use without hampering the operation of the scalpel meanwhile aiding the surgeon. It can be thought of as a handle or clamping system for the fiber. One such device would be made of two sections which screw together. As the two parts screw together they would clamp or pinch onto the fiber itself. Thus, the positioning device would be attached to the fiber and would be convenient for manipulating the firing tip precisely. The device could also have a fine adjustment for metering a precise length of fiber through the positioning device.

FIG. 2 is a cross section view of a preferred embodiment of the firing tip 20. At the end of the firing tip on each side there is a crimp 22 for securing the firing tip to the optical fiber 12. It will be understood by those skilled in the art that other means of attachment, such as adhesives or clamps may be used.

FIG. 2 also shows the hollow body portion 24 of the firing tip 20. The hollow body portion of the tip has a distal end 26. Assembly of the firing tip involves placing the reflective insert member 30 inside the hollow body portion. The distal end of the firing tip is formed so as to provide a smooth surface. This can be done by various means, such as mechanical compression, grinding, polishing or coating the tip. The tip can be rounded to provide ease in operation.

The reflective surface 32 of the inserted member can be formed in various ways, including deposition, plating or sputtering with a reflective material (such as gold) upon the surface of the insert, mechanically compressing, grinding or polishing the insert, or other means known by those skilled in the art. The highly reflective surface of the insert permits very efficient transmission of the incident laser beam. Thus, very little of the incident radiation is absorbed by the insert member and overheating of the firing tip is prevented.

The hollow body portion is constructed out of a durable, heat-withstanding material, such as stainless steel. Thus, as the insert is unavoidably heated to some extent by the incident radiant energy, the shape and integrity of the insert is maintained by the more durable firing tip body. FIG. 2 also shows a machined boss 40 on the insert as well as a machined shoulder 42 on the inside surface of the central hollow body portion. When the boss is biased against the shoulder and the distal end of the hollow body portion is compressed around the insert member the insert member is held firmly in place.

Also shown in FIG. 2 is a cooling vent 44. More than one cooling vent can be placed in this section of the hollow body portion. As the incident radiation is reflected out the firing window opening 46 of the firing tip the insert member becomes heated. As discussed above, a cooling solution is constantly used to irrigate the area being operated on. Thus, by a convective process, the cooling liquid is drawn through the cooling vents into the body portion. As the liquid is vaporized at the hot reflective surface of the insert, steam is generated normal to the reflective surface and escapes either through the cooling vent itself or through the firing window opening.

Figure 3:
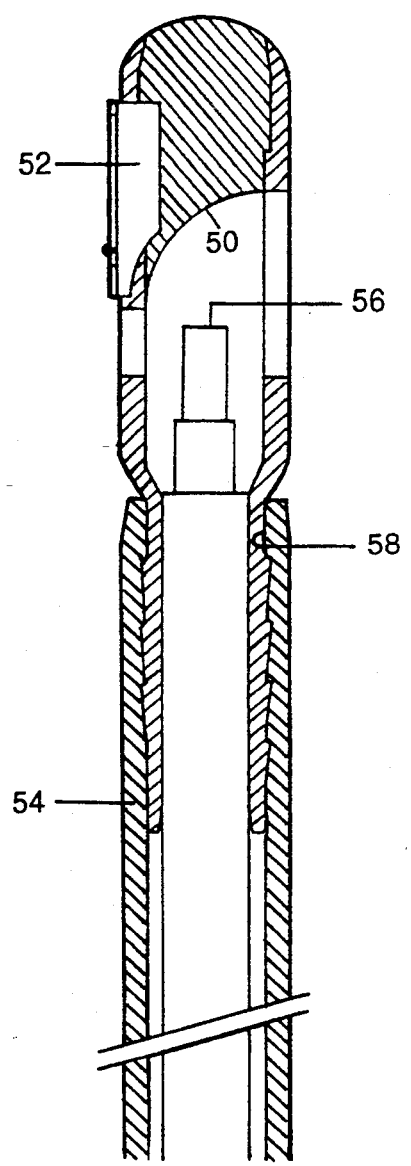
FIG. 3 is a cross section view of another embodiment of the firing tip showing both a concave reflective surface and a slidable shutter for closing the cooling vent FIGS. 4A, 4B and 4C varying angles of reflection.

FIG. 3 is a cross section view of another preferred embodiment of the firing tip. In this embodiment, the reflective surface 50 of the insert is somewhat concave, having a rounded or parabolic curvature. This feature allows the firing tip to be used either as a cutting or as a coagulating tool. The radiant energy beam impinges on the reflective surface, in a roughly elliptical pattern which is similar to that of the flat reflective surface embodiment. Then the beam is reflected into a cone shape, narrowing through a focal region, and thereafter widening. By increasing the radius of curvature of the concavity, the focal point of the incident beam can be extended to points farther away from the firing window of the firing tip. With this invention it is possible to provide the surgeon with a range of focal length tools.

In the embodiment of FIG. 3, the cooling vents have a movable shutter 52. The shutter can be manually moved into a position covering part or all of the cooling vent. This could also be a screen or cap, or other means known by those skilled in the art, to increase or restrict the cooling fluid flow rate through the cooling vents.

FIG. 3 also shows an embodiment of the invention with the firing tip secured to a cannula. This semi-rigid tube shaped piece 54 covers the fiber which extends from the end of the cannula member and is positioned such that the transmitting end of the waveguide 56 directly adjacent to the reflecting surface 50 of the firing tip. The attachment means 58 is shown here as a machined barbed end which engages the semi-rigid cannula member. It will be understood by those skilled in the art that alternative attachment means, such as adhesives or clamps, could also be used.

Figure 4A:
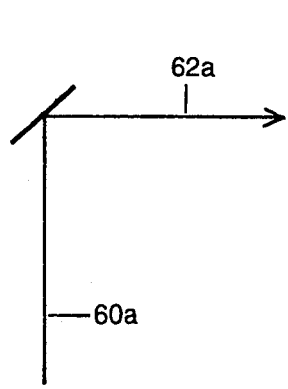
Figure 4B:
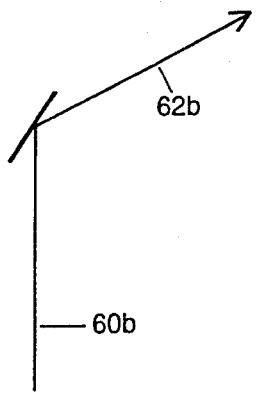
Figure 4C:
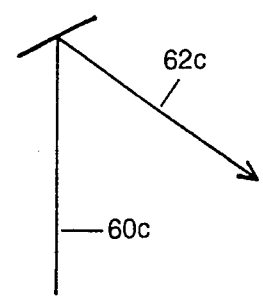

FIGS. 4A-C show how the angle of reflectance of a laser beam can be varied according to the angles at which the reflective surface is positioned. The figures show the incident beams 60a, 60b, 60c and the beam paths after reflectance 62a, 62b, 62c. It is possible to vary the angle at which the reflective surface lies with respect to the axis of the insert. Thus, it is possible to build laser scalpels which reflect the incident laser beam at approximately a 90 degree angle (FIG. 4A), angles less than 90 degrees (FIG. 4B) and angles greater than 90 degrees (FIG. 4C) with respect to the central axis. There is a minimum angle which must not be exceeded, beyond which the reflected energy would begin to have a destructive effect upon the firing tip itself.

Figure 5A:
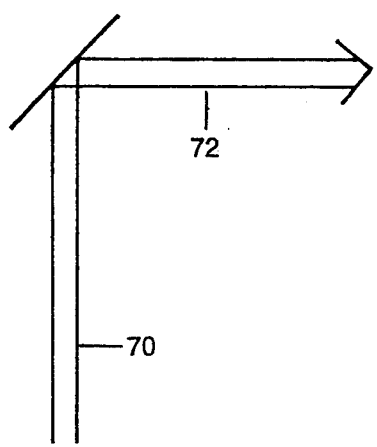
FIGS. 5A and 5B show two different beam paths generated by two different embodiments of the firing tip insert member.
Figure 5B:
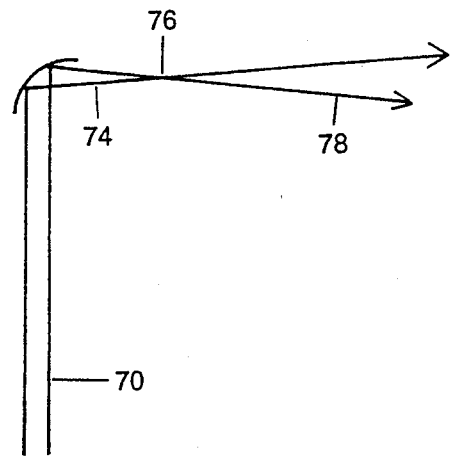

FIGS. 5A and B are representations of the incident and reflected beam patterns which would be produced by the two embodiments of the firing tip insert members of FIGS. 2 and 3. In both embodiments the incident beam impinges upon the reflective surface in a somewhat elliptical pattern. In FIG. 5a the reflected radiant energy forms a beam which, at a point near the flat reflective surface, is nearly as large in diameter as the incident beam but which is slightly divergent thereafter. This embodiment could be used in a surgical application where tissue cutting or ablation is desired, as the intensity of the beam is fairly uniform throughout its length and is narrowly focused In FIG. 5b the reflected beam is cone shaped, narrowing or converging through a region corresponding with the focal point of the reflective surface, and thereafter. The cross section area of the beam path near the focal point is very small. Thus, cutting or tissue ablation is possible when the scalpel of FIG. 3 is positioned so that the laser beam impinges upon the tissue at a point in the focal region of the radiant beam. However, this embodiment may also be effective for coagulating tissue if the scalpel is positioned in such a way as to allow the reflected beam to impinge upon the tissue at a point somewhat between the reflective surface and the focal region or, alternatively, at a point somewhat beyond the focal region. Thus, this embodiment of the invention can be used for coagulation of tissue and then for tissue removal or incision.

Figure 6A:
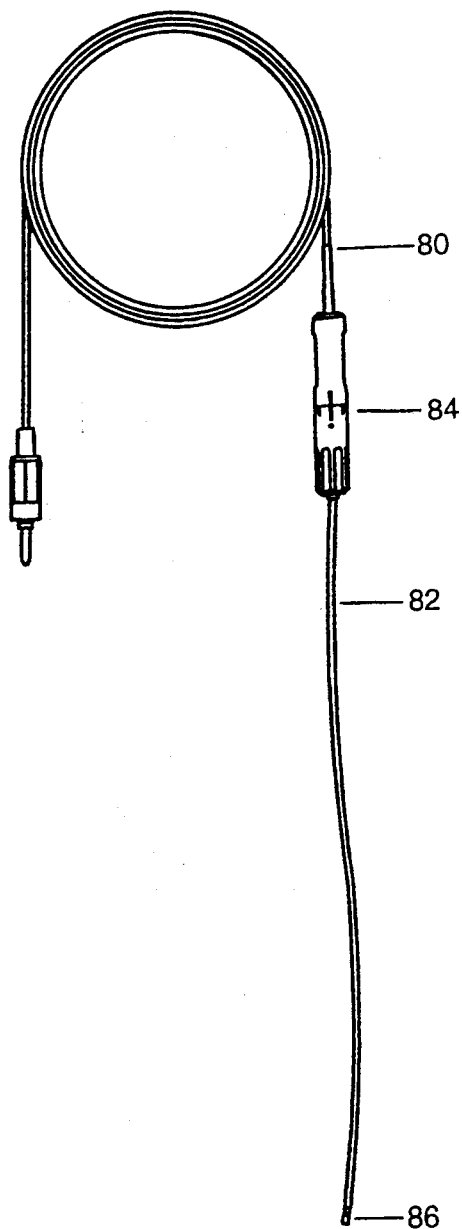
FIG. 6A is a view of the firing tip mounted on a semi-rigid cannula with the optical fiber extending through and having an indexed side positioning device attached.
Figure 6B:
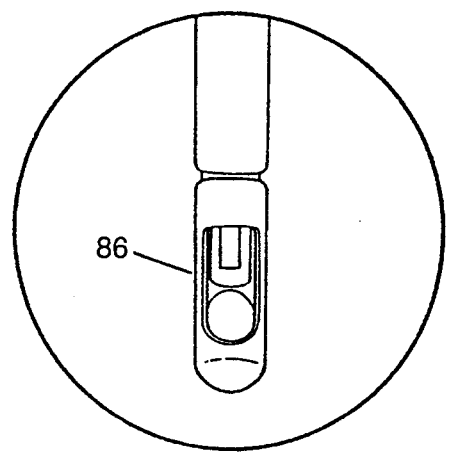
FIG. 6B is a front detail of an embodiment of the firing tip of the present invention.

In FIG. 6 another preferred embodiment is shown. Here, the optical fiber 80 would slide into a rigid cannula member 82 with a rotatable indexed locking device 84 mounted at the end opposite the firing tip 86, shown enlarged, which would lock onto the fiber cladding. Such a locking device could be indexed so as to twist and lock into fixed positions axially around the fiber. The cannula member could even be semi-flexible in that it could bend a certain amount but rigid with respect to maintaining it's hollow, tubular shape. The firing tip is essentially as is described above with respect to the embodiment shown in FIG. 3. The cannula member could be made detachably attached to the indexed position locking device. This embodiment of the invention is useful for operations using a cystoscope or other endoscope. The entire cannula member turns about the internal fiber. The positioning means, similar to that of the embodiment of FIG. 2, would allow the fiber to be inserted into the cannula member and tightened into place. Then, the cannula member would rotate about the fiber in order to direct the firing window opening toward the intended region.

The embodiments of this invention can be used for various operations, including coagulating, incising or removing tissue. The invention can be used with an endoscope with or without a separate lumen for the scalpel itself. The tissue to be removed can first be coagulated and then vaporized. A shutter or screen on the cooling vent on the firing tip can be adjusted for service in a coagulating mode or service in a vaporizing mode.

As disclosed in application Ser. No. 07/265,565, filed Nov. 1, 1988, now U.S. Pat. No. 4,950,268, issued Aug. 21, 1990 to John Rink, which is incorporated herein by reference, a laser driver and control circuit can be obtained which will produce a pulsed, high-peak power laser. Using such a laser source, a scalpel can be used to coagulate tissue using a power output of approximately 30-50 watts. Then, the power output of the laser can be increased to approximately 60-80 watts and the coagulated tissue can be vaporized. The scalpel of this invention comprises cooling vents on the scalpel firing tip to prevent overheating of the tip. Convective cooling by the irrigation cooling fluid being used takes place through these vents. It may be advantageous to reduce the flow of cooling fluid through the firing tip during the vaporization step of the operation because the cooling fluid would also have the effect of cooling the affected tissue and preventing vaporization. The exact parameters of the operation muse be chosen by the surgeon who has ultimate control over power output, scalpel design, degree of cooling fluid flow, etc.

Figure 7:
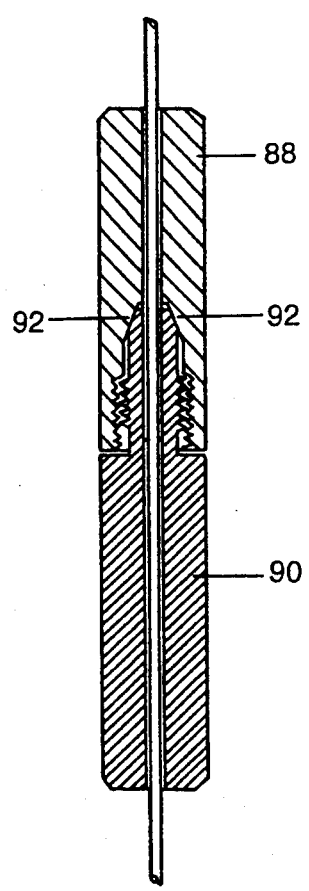
FIG. 7 is a cross section detail view of an embodiment of the slidable positioning device of the present invention.

FIG. 7 shows the positioning device indicated by reference numeral 18 in FIG. 1. As discussed earlier the two parts of the device 88 and 90 screw together with the fiber passing directly through the central of the two parts. As part 88 threads onto part 90, the tip of part 90 inside part 88 is compressed about the fiber at 92. As the compression is increased the device becomes locked onto the fiber. Thus, this positioning device allows the depth of insertion of the fiber into an external endoscope to be determined precisely. The locking means described is one embodiment and other locking means would be known to those familiar with the art.

Figure 8:
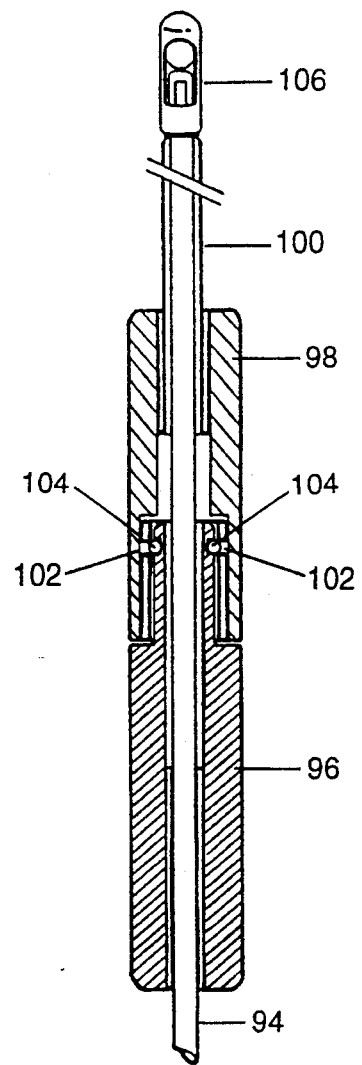
FIG. 8 is a cross section detail view of an embodiment of the indexed locking rotable coupling means device of the present invention.

FIG. 8 shows the indexed locking device shown in FIG. 6 as reference numeral 84. As described there, the optical fiber 94 is shown passing through the two main parts of the device, an inner member 96 and a sleeve member 98. The rigid cannula member 100 is attached to sleeve 98. Inner member 96 locks onto the fiber while part 98 rotates about the fiber. At points 102 there are small indentations or slots located circumferentially around the inside of sleeve 98. Small stubs or key elements 104 located on the external surface of inner member 96 engage the slots of part 98, thus locking the two parts 96 and 98 together. As sleeve 98, coupled to the cannula member, is rotated about the fiber, the regularly spaced slots in part 98 selectively the small stubs. Thus, a series of 6 regularly spaced slots in sleeve 98 will result in 6 indexed positioned of rotation of the device. A different number of slots can be used to increase or decrease the degree of selectivity desired. As the cannula member is twisted into different positions, the firing window 106 (part of the firing tip of the cannula member) changes orientation and direction of fire. Only one possibility for the structure of the indexed rotatable coupling means is described here. Various embodiments of the indexed rotatable coupling means would be obvious to those skilled in the art.

We claim:

1. An improved angle firing fiber optic surgical scalpel for cutting and coagulating tissue by means of radiant energy, said scalpel comprising:
a fiber optic waveguide having a receiving end and a transmitting end;
and a firing tip, said firing tip comprising:
an attachment means for attaching said firing tip to said transmitting end of said waveguide;
a central hollow body portion having a distal end, a proximal end and a central axis, said attachment means attaching said central hollow body portion of said firing tip to said waveguide at said proximal end, said central hollow body portion partially cut away defining an opening, said central hollow body portion further having an internal circumferential shoulder located at a point intermediate between said opening and said distal end of said central hollow body portion, said central hollow body portion further comprising at least one cooling vent, said waveguide capable of transmitting radiant energy along said central axis towards said distal end;
and an insert member axially disposed within said central hollow body portion having a first end and a second end, said second end being adjacent to said distal end of said central hollow body portion, said insert member further having a circumferential boss at a point intermediate between said first end and said second end, said boss in contact with said shoulder of said central hollow body portion, said first end having a highly reflective surface, said highly reflective surface being positioned within said central hollow body portion of said firing tip in an operative position reflecting said radiant energy through said opening at an operative angle with respect to said central axis.

2. The invention of claim 1 wherein said highly reflective surface of said insert member is positioned within said central hollow body portion such that radiant energy is reflected at an angle of 90 degrees with respect to said central axis through said opening.

3. The invention of claim 1 wherein said highly reflective surface of said insert member is positioned within said central hollow body portion of said firing tip such that radiant energy is reflected at an angle of greater than 90 degrees with respect to said central axis through said opening.

4. The invention of claim 1 wherein said highly reflective surface of said insert member is positioned within said central hollow body portion of said firing tip such that radiant energy is reflected at an angle of less than 90 degrees with respect to said central axis through said opening.

5. The invention of claim 1 wherein said receiving end of said waveguide further comprises a means for coupling said waveguide to a source of radiant energy.

6. The invention of claim 1 further comprising a positioning device, said positioning device having a locking means for attaching said positioning device to said waveguide at a point intermediate the receiving end of said waveguide and said attachment means.

7. The invention of claim 1 wherein said central hollow body portion comprises an elongated cannula with a proximal end and a distal end, said proximal end having a position locking means detachably locked to said waveguide, said firing tip attached to said distal end by said attachment means.

8. The invention of claim 1 wherein said highly reflective surface is planar.

9. The invention of claim 1 wherein said highly reflective surface is concave.

10. The invention of claim 1 further comprising a flowrate restricting means for restricting cooling fluid flow through said cooling vent movably attached to said central hollow body portion adjacent to said cooling vent.

11. An improved angle firing fiber optic surgical scalpel for cutting and coagulating tissue by means of radiant energy, said scalpel comprising:
a fiber optic waveguide having a receiving end and a transmitting end;
a rigid cannula member, said cannula member having a proximal end and a distal end, said waveguide being axially disposed within said cannula member such that the transmitting end of said waveguide is adjacent to said distal end of said cannula member;
a waveguide locking means adjacent to said proximal end of said cannula member for locking said waveguide within said cannula member thereby maintaining said transmitting end of said waveguide adjacent to said distal end of said cannula member;
and a firing tip, said firing tip comprising:
an attachment means attaching said firing tip to the distal end of said cannula member;
a central hollow body portion having a distal end, a proximal end and a central axis, said attachment means attaching said proximal end of said central hollow body portion of said firing tip to said distal end of said cannula member, said central hollow body portion further having an internal circumferential shoulder located at a point intermediate between said attachment means and said distal end of said central hollow body portion, said central hollow body portion having at least one cooling vent, said waveguide capable of transmitting radiant energy along said central axis toward the distal end of said central hollow body portion, said central hollow body portion defining an opening;
and an insert member axially disposed within said central hollow body portion having a first end and a second end, said second end being adjacent to the distal end of said central hollow body portion, said insert member further having a circumferential boss at a point intermediate between said exposed end and said second end, said boss in contact with said shoulder of said central hollow body portion, said first end having a highly reflective surface, said highly reflective surface being positioned within said central hollow body portion of said firing tip in an operative position reflecting said radiant energy through said opening at an operative angle with respect to said central axis.

12. The invention of claim 11 wherein said highly reflective surface of said insert member is positioned within said central hollow body portion such that radiant energy is reflected at an angle of 90 degrees with respect to said central axis through said opening.

13. The invention of claim 11 wherein said highly reflective surface of said insert member is positioned within said central hollow body portion of said firing tip such that radiant energy is reflected at an angle of greater than 90 degrees with respect to said central axis through said opening.

14. The invention of claim 11 wherein said highly reflective surface of said insert member is positioned within said central hollow body portion of said firing tip such that radiant energy is reflected at an angle of less than 90 degrees with respect to said central axis through said opening.

15. The invention of claim 11 wherein said proximal end of said cannula member comprises a rotatable coupling means for coupling said cannula member to said waveguide locking means and allowing rotation of said cannula member about said waveguide.

16. The invention of claim 11 wherein said rotatable coupling means comprises an inner member disposed within a sleeve, said inner member having a plurality of small stubs, said sleeve having a plurality of slots, and said inner member rotating within said sleeve into a plurality of predetermined indexed positions by engagement of said small stubs on said inner member and said slots within said sleeve.

17. The invention of claim 12 wherein said proximal end of said waveguide further comprises a means for coupling said waveguide to a source of radiant energy.

18. The invention of claim 11 wherein said highly reflective surface is planar.

19. The invention of claim 11 wherein said highly reflective surface is concave.

20. The invention of claim 11 further comprising an adjustable flowrate restricting means for restricting cooling fluid flow through said cooling vent movably attached to said central hollow body portion adjacent to said cooling vent.

21. An improved angle firing fiber optic surgical scalpel for cutting and coagulating tissue by means of radiant energy, said scalpel comprising:
a fiber optic waveguide having a receiving end and a transmitting end;
and a firing tip, said firing tip comprising:
an attachment means for attaching said firing tip to said waveguide, said attachment means comprising a rotatable position locking means detachably locked to said waveguide;
a central hollow body portion comprising an elongated cannula section having a distal end, a proximal end and a central axis, said position locking means attaching said central hollow body portion to said waveguide at said proximal end of said cannula section such that said waveguide is disposed within said cannula section, said firing tip attached to said distal end by said attachment means said central hollow body portion partially cut away defining an opening, said central hollow body portion further comprising at least one cooling vent, said waveguide capable of transmitting radiant energy along said central axis toward said distal end;
and an insert member axially disposed within said central hollow body portion having a first end and a second end, said second end being adjacent to said distal end of said elongated cannula member of said central hollow body portion, said first end having a highly reflective surface, said highly reflective surface being positioned within said central hollow body portion of said firing tip in an operative position reflecting said radiant energy through said opening at an operative angle with respect to said central axis.

22. An improved angle firing fiber optic surgical scalpel for cutting and coagulating tissue by means of radiant energy, said scalpel comprising:
a fiber optic waveguide having a receiving end and a transmitting end;
a rigid cannula member, said cannula member having a proximal end and a distal end, said waveguide being axially disposed within said cannula member such that the transmitting end of said waveguide is adjacent to said distal end of said cannula member;
a waveguide locking means adjacent to said proximal end of said cannula member for locking said waveguide within said cannula member thereby maintaining said transmitting end of said waveguide adjacent to said distal end of said cannula member, said proximal end of said cannula member comprising a rotatable coupling means for coupling said cannula member to said waveguide locking means and allowing rotation of said cannula member about said waveguide, said rotatable coupling means comprising an inner member disposed within a sleeve, said inner member having a plurality of small stubs, said sleeve having a plurality of slots, and said inner member rotating within said sleeve into a plurality of predetermined indexed positions by engagement of said small stubs on said inner member and said slots within said sleeve;
and a firing tip, said firing tip comprising:
an attachment means attaching said firing tip to the distal end of said cannula member;
a central hollow body portion having a distal end, a proximal end and a central axis, said attachment means attaching said proximal end of said central hollow body portion of said firing tip to said distal end of said cannula member, said central hollow body portion having at least one cooling vent, said waveguide capable of transmitting radiant energy along said central axis toward the distal end of said central hollow body portion, said central hollow body portion defining an opening;
and an insert member axially disposed within said central hollow body portion having a first end and a second end, said second end being adjacent to the distal end of said central hollow body portion, said first end having a highly reflective surface, said highly reflective surface being positioned within said central hollow body portion of said firing tip in an operative position reflecting said radiant energy through said opening at an operative angle with respect to said central axis.

* * * * *